US008504149B2

(12) United States Patent
Libbus et al.

(10) Patent No.: US 8,504,149 B2
(45) Date of Patent: Aug. 6, 2013

(54) SYSTEM AND METHOD TO DELIVER THERAPY IN PRESENCE OF ANOTHER THERAPY

(75) Inventors: Imad Libbus, St. Paul, MN (US); Andrew P. Kramer, Marine on St. Croix, MN (US); William J. Linder, Golden Valley, MN (US); Jeffrey E. Stahmann, Ramsey, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 13/397,115

(22) Filed: Feb. 15, 2012

(65) Prior Publication Data

US 2012/0150250 A1 Jun. 14, 2012

Related U.S. Application Data

(62) Division of application No. 12/148,843, filed on Apr. 23, 2008, now Pat. No. 8,131,359, which is a division of application No. 11/125,503, filed on May 10, 2005, now Pat. No. 7,493,161.

(51) Int. Cl.
*A61N 1/05* (2006.01)

(52) U.S. Cl.
USPC .................................................. 607/4; 607/2

(58) Field of Classification Search
USPC ............................................... 607/2, 4, 9, 14
See application file for complete search history.

(56) References Cited

U.S. PATENT DOCUMENTS 4,201,219 A 5/1980 Bozal Gonzalez
4,791,931 A 12/1988 Slate
4,960,129 A 10/1990 dePaola et al.
5,111,815 A 5/1992 Mower
5,199,428 A 4/1993 Obel et al.
5,203,326 A 4/1993 Collins
5,318,592 A 6/1994 Schaldach
5,330,507 A 7/1994 Schwartz
5,334,221 A 8/1994 Bardy (Continued)

FOREIGN PATENT DOCUMENTS

EP 0547734 A2 6/1993
EP 1421973 A2 5/2004

(Continued)

OTHER PUBLICATIONS

"U.S. Appl. No. 11/125,503, Notice of Allowance mailed Jan. 4, 2008", 8 pgs.

(Continued)

*Primary Examiner* — Brian T Gedeon
(74) *Attorney, Agent, or Firm* — Schwegman Lundberg & Woeesner, P.A.

(57) ABSTRACT

Various aspects relate to a method. In various embodiments, a therapy of a first therapy type is delivered, and it is identified whether a therapy of a second therapy type is present to affect the therapy of the first therapy type. Delivery of the therapy is controlled based on the presence of the therapy of the second therapy type. Some embodiments deliver the therapy of the first type using one set of parameters in the presence of a therapy of a second type, and deliver the therapy of the first type using another set of parameters when the therapy of the second type is not present. In various embodiments, one of the therapy types includes a cardiac rhythm management therapy, and the other includes a neural stimulation therapy. Other aspects and embodiments are provided herein.

25 Claims, 10 Drawing Sheets

855
856 CONTROLLER
861 THERAPY(IES) OF THERAPY TYPE 1
862 MODE USING PARAMETER SET 1 ABSENT PRESENCE OF A TYPE 2 THERAPY
863 MODE USING PARAMETER SET 2 WITH PRESENCE OF A TYPE 2 THERAPY
857 STIMULATOR CIRCUITRY
858 PORT(S)
859 LEAD(S) WITH ELECTRODE(S)
860 INDICATOR OF PRESENCE OF A TYPE 2 THERAPY

U.S. PATENT DOCUMENTS 5,356,425 A 10/1994 Bardy et al.
5,411,531 A 5/1995 Hill et al.
5,507,784 A 4/1996 Hill et al.
5,522,854 A 6/1996 Ideker et al.
5,578,061 A 11/1996 Stroetmann et al.
5,626,621 A 5/1997 Skoglund et al.
5,662,689 A 9/1997 Elsberry et al.
5,690,681 A 11/1997 Geddes et al.
5,792,187 A 8/1998 Adams
5,817,131 A 10/1998 Elsberry et al.
5,893,881 A 4/1999 Elsberry et al.
5,916,239 A 6/1999 Geddes et al.
5,928,272 A 7/1999 Adkins et al.
6,006,134 A 12/1999 Hill et al.
6,073,048 A 6/2000 Kieval et al.
6,134,470 A 10/2000 Hartlaub
6,240,314 B1 5/2001 Plicchi et al.
6,341,236 B1 1/2002 Osorio et al.
6,415,183 B1 7/2002 Scheiner et al.
6,466,822 B1 10/2002 Pless
6,477,418 B2 11/2002 Plicchi et al.
6,511,500 B1 1/2003 Rahme
6,522,926 B1 2/2003 Kieval et al.
6,622,041 B2 9/2003 Terry, Jr. et al.
6,668,191 B1 12/2003 Boveja
6,934,583 B2 8/2005 Weinberg et al.
6,937,896 B1 8/2005 Kroll
7,123,961 B1 10/2006 Kroll et al.
7,260,431 B2 8/2007 Libbus et al.
7,277,761 B2 10/2007 Shelchuk
7,299,086 B2 11/2007 McCabe et al.
7,493,161 B2 2/2009 Libbus et al.
7,542,800 B2 6/2009 Libbus et al.
7,570,999 B2 8/2009 Libbus et al.
7,587,238 B2 9/2009 Moffitt et al.
7,657,312 B2 2/2010 Pastore et al.
7,660,628 B2 2/2010 Libbus et al.
7,873,413 B2 1/2011 McCabe et al.
2002/0107553 A1 8/2002 Hill et al.
2002/0165586 A1 11/2002 Hill et al.
2003/0004549 A1 1/2003 Hill et al.
2003/0045909 A1 3/2003 Gross et al.
2003/0060848 A1 3/2003 Keival et al.
2003/0060857 A1 3/2003 Perrson et al.
2003/0060858 A1 3/2003 Kieval et al.
2003/0074039 A1 4/2003 Puskas
2003/0078623 A1 4/2003 Weinberg et al.
2003/0100924 A1 5/2003 Foreman et al.
2003/0149450 A1 8/2003 Mayberg
2003/0153953 A1 8/2003 Park et al.
2003/0181951 A1 9/2003 Cates
2003/0212445 A1 11/2003 Weinberg
2003/0229380 A1 12/2003 Adams et al.
2004/0082980 A1 4/2004 Mouine et al.
2004/0088009 A1 5/2004 Degroot
2004/0133248 A1 7/2004 Frei et al.
2004/0138721 A1 7/2004 Osorio et al.
2004/0162594 A1 8/2004 King
2004/0172074 A1 9/2004 Yoshihito
2004/0172075 A1 9/2004 Shafer et al.
2004/0193231 A1 9/2004 David et al.
2004/0199210 A1 10/2004 Shelchuk
2004/0215289 A1 10/2004 Fukui
2005/0060001 A1 3/2005 Singhal et al.
2005/0096705 A1 5/2005 Pastore et al.
2005/0143779 A1 6/2005 Libbus
2005/0143785 A1 6/2005 Libbus
2005/0149126 A1 7/2005 Libbus
2005/0149127 A1 7/2005 Libbus
2005/0149128 A1 7/2005 Heil, Jr. et al.
2005/0149129 A1 7/2005 Libbus et al.
2005/0149130 A1 7/2005 Libbus
2005/0149131 A1 7/2005 Libbus et al.
2005/0149132 A1 7/2005 Libbus
2005/0149133 A1 7/2005 Libbus et al.
2005/0149143 A1 7/2005 Libbus et al.
2005/0149148 A1 7/2005 King
2005/0149156 A1 7/2005 Libbus et al.
2005/0251216 A1 11/2005 Hill et al.
2005/0261741 A1 11/2005 Libbus et al.
2006/0020297 A1 1/2006 Gerber et al.
2006/0052831 A1 3/2006 Fukui
2006/0079945 A1 4/2006 Libbus
2006/0095080 A1 5/2006 Libbus et al.
2006/0106429 A1 5/2006 Libbus et al.
2006/0116737 A1 6/2006 Libbus
2006/0167497 A1 7/2006 Armstrong et al.
2006/0206153 A1 9/2006 Libbus et al.
2006/0206154 A1 9/2006 Moffitt et al.
2006/0206159 A1 9/2006 Moffitt et al.
2006/0217772 A1 9/2006 Libbus et al.
2006/0224188 A1 10/2006 Libbus et al.
2006/0224202 A1 10/2006 Moffitt et al.
2006/0241699 A1 10/2006 Libbus et al.
2006/0241725 A1 10/2006 Libbus et al.
2006/0259083 A1 11/2006 Libbus et al.
2006/0271118 A1 11/2006 Libbus et al.
2007/0021799 A1 1/2007 Kieval et al.
2007/0142864 A1 6/2007 Libbus et al.
2007/0142871 A1 6/2007 Libbus et al.
2008/0015648 A1 1/2008 Libbus et al.
2011/0137360 A1 6/2011 Ternes

FOREIGN PATENT DOCUMENTS

EP 1421973 A3 5/2004
EP 1426078 A1 6/2004
JP 2004173791 A 6/2004
JP 2004351122 A 12/2004
JP 2005500863 A 1/2005
WO WO-9216257 A1 10/1992
WO WO-03011388 A2 2/2003
WO WO-03018108 A3 3/2003
WO WO-03076008 A1 9/2003
WO WO-03099377 A1 12/2003
WO WO-2004084993 A1 10/2004
WO WO-2004110549 A2 12/2004
WO WO-2005042091 A1 5/2005
WO WO-2006055436 A1 5/2005
WO WO-2005063332 A1 7/2005
WO WO-2005113066 A1 12/2005
WO WO-2006121929 A1 11/2006
WO WO-2007078410 A1 7/2007

OTHER PUBLICATIONS

"U.S. Appl. No. 11/125,503, Examiner Interview Summary mailed Oct. 18, 2007", 4 pgs.
"U.S. Appl. No. 11/125,503, Non-Final Office Action mailed Jun. 28, 2007", 8 pgs.
"U.S. Appl. No. 11/125,503, Notice of Allowance mailed Mar. 8, 2007", 8 pgs.
"U.S. Appl. No. 11/125,503, Response filed Oct. 29, 2007 to Non Final Office Action mailed Jun. 28, 2007", 21 pgs.
"U.S. Appl. No. 11/312,178, Non-Final Office Action mailed May 14, 2008", 6 pgs.
"U.S. Appl. No. 11/312,178, Notice of Allowance mailed Apr. 3, 2009", 6 pgs.
"U.S. Appl. No. 11/312,178, Notice of Allowance mailed Nov. 14, 2008", 6 pgs.
"U.S. Appl. No. 11/312,178, Preliminary Amendment filed Mar. 14, 2006", 7 pgs.
"U.S. Appl. No. 11/312,178, Response filed Aug. 14, 2008 to Non Final Office Action mailed May 14, 2008", 14 pgs.
"U.S. Appl. No. 12/148,843, Non Final Office Action mailed May 31, 2011", 8 pgs.
"U.S. Appl. No. 12/148,843, Notice of Allowance mailed Oct. 27, 2011", 10 pgs.
"U.S. Appl. No. 12/148,843, Response filed Aug. 30, 2011 to Non Final Office Action mailed May 31, 2011", 9 pgs.
"U.S. Appl. No. 12/148,843, Response filed Apr. 14, 2011 to Restriction Requirement mailed Mar. 15, 2011", 10 pgs.
"U.S. Appl. No. 12/148,843, Restriction Requirement mailed Mar. 15, 2011", 9 pgs.
"European Application Serial No. 06752356.3, Office Action mailed Apr. 1, 2008", 6 pgs.

"European Application Serial No. 06752356.3, Response filed Sep. 11, 2008 to Communication mailed Apr. 1, 2008", 17 pgs.
"European Application Serial No. 06827323.4, Communication mailed Jun. 2, 2009", 2 pgs.
"European Application Serial No. 06827323.4, Communication mailed Nov. 12, 2008", 3 pgs.
"European Application Serial No. 06827323.4, Response filed Apr. 24, 2009 to Communication mailed Nov. 12, 2008", 6 pgs.
"European Application Serial No. 06827323.4, Summons to Attend Oral Proceedings mailed May 19, 2010", 3 pgs.
"European Application Serial No. 06827323.4, Written Submissions filed Sep. 23, 2010", 4 pgs.
"International Application Serial No. PCT/US2006/017539, International Search Report and Written Opinion mailed Sep. 1, 2006", 12 pgs.
"International Application Serial No. PCT/US2006/042727, International Search Report and Written Opinion mailed Apr. 23, 2007", 16 pgs.
"Japanese Application Serial No. 2008-511206, Office Action mailed Nov. 11, 2011", With English Translation, 7 pgs.
Bilgutay, A M, et al., "A new concept in the treatment of hypertension utilizing an implantable electronic device: "Baropacer"", Trans Am Soc Artif Intern Organs., 10, (1964), 387-395.
Li, M., et al., "Vagal nerve stimulation markedly improves long-term survival after chronic heart failure in rats", Circulation, 109(1), (2004), 120-124.
Libbus, Imad, "Implantable Device for Treating Epilepsy and Cardiac Rhythm Disorders", U.S. Appl. No. 11/312,178, filed Dec. 21, 2005, 39 pgs.
McGregor, A., et al., "Right-Sided Vagus Nerve Stimulation as a Treatment for Refractory Epilepsy in Humans", Epilepsia; 46(1), (Jan 2005), 91-96.
Rugg-Gunn, F. J, et al., "Cardiac arrhythmias in focal epilepsy: a prospective long-term study.", Lancet, 364(9452), (Dec. 18-31, 2004), 2212-9.
Sigurdsson, A., et al., "The Role of Neurohormonal Activation in Chronic Heart Failure and Postmyocardial Infarction", American Heart Journal, 132(1, Part 2), (Jul. 1996), 229-234.
Vanoli, E., et al., "Vagal Stimulation and Prevention of Sudden Death in Conscious Dogs With a Healed Myocardial Infarction", Circulation Research, 68(5), (May 1991), 1471-1481.

SYSTEM AND METHOD TO DELIVER THERAPY IN PRESENCE OF ANOTHER THERAPY

CLAIM OF PRIORITY

This application is a divisional of U.S. application Ser. No. 12/148,843, filed Apr. 23, 2008, now issued as U.S. Pat. No. 8,131,359, which is a divisional of U.S. application Ser. No. 11/125,503, filed May 10, 2005, now U.S. Pat. No. 7,493,161, the specifications of which are herein incorporated by reference.

TECHNICAL FIELD

This application relates generally to medical devices and, more particularly, to systems, devices and methods to control the delivery of therapy.

BACKGROUND

Different types of therapies can be delivered simultaneously, or near simultaneously, to treat the same condition or to treat different conditions. For example, it possible to deliver both neural stimulation (NS) therapy and cardiac rhythm management (CRM) therapy.

Some NS therapy can alter cardiac contractility and excitability. Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, have been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction.

SUMMARY

Various aspects of the present subject matter relate to a device. In various embodiments, the device comprises at least one port to connect to at least one lead with at least one electrode, stimulator circuitry connected to the at least one port and adapted to deliver electrical pulses to at least one of the electrodes as part of a first electrical therapy type, and a controller connected to the stimulator circuitry. The controller is adapted to control delivery of the electrical pulses using a plurality of parameters for at least one programmed electrical therapy of the first electrical therapy type. The controller is adapted to determine when a therapy of a second electrical therapy type is applied, provide electrical therapy for the first electrical therapy type using a first set of parameters when the therapy of the second electrical therapy type is present to affect the at least one programmed electrical therapy for the first electrical therapy type, and provide electrical therapy using a second set of parameters when the therapy of the second electrical therapy type is not present.

Various aspects of the present subject matter relate to a method. In various embodiments, a therapy of a first therapy type is delivered, and it is identified whether a therapy of a second therapy type is present to affect the therapy of the first therapy type. Delivery of the therapy is controlled based on the presence of the therapy of the second therapy type. Some embodiments deliver the therapy of the first type using one set of parameters in the presence of a therapy of a second type, and deliver the therapy of the first type using another set of parameters when the therapy of the second type is not present.

In various embodiments, the first therapy type includes a cardiac rhythm management therapy, and the second therapy type includes a neural stimulation therapy. In various embodiments, the first therapy type includes a neural stimulation therapy and the second therapy type includes a cardiac rhythm management therapy.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
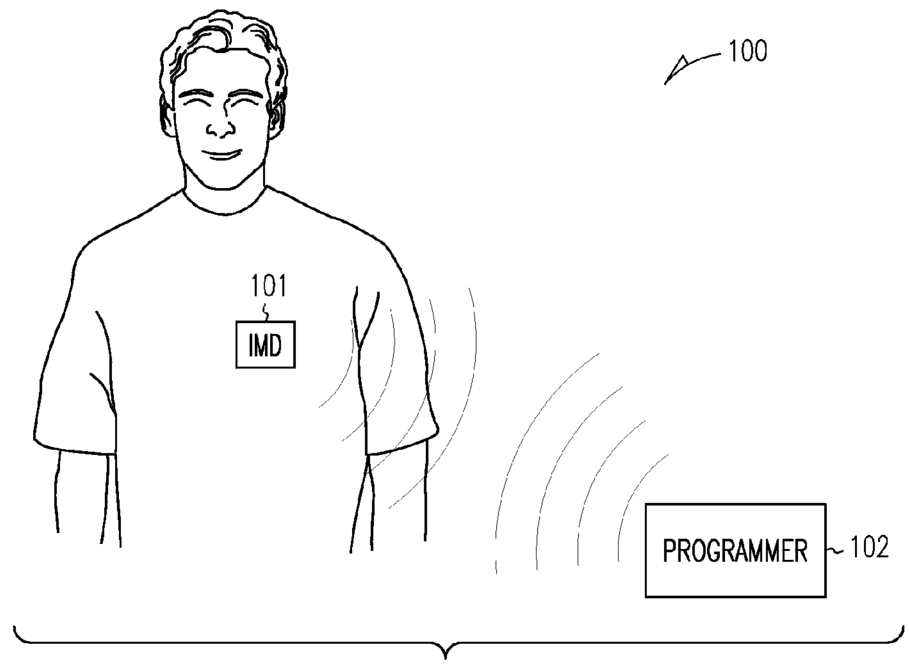
FIG. 1 illustrates a system including an implantable medical device (IMD) and a programmer, according to various embodiments.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The present subject matter relates to a device that delivers a therapy of a first therapy type, identifies whether a therapy of a second therapy type is present to affect the therapy of the first therapy type, and controls delivery of the therapy based on the presence of the therapy of the second therapy type and based on a plurality of parameters organized into a first set and a second set in at least one programmed therapy for the therapy type. Some embodiments of the present subject matter relates to a device that provides a cardiac rhythm management (CRM) type of therapy, such as a pacing therapy and various pacing modes, a defibrillation therapy, and a cardiac resynchronization therapy (CRT), and combinations thereof. The CRM type of therapy is provided in the presence of neural stimulation (NS) therapy. The CRM and NS therapy can be contained in the same device or in independent implantable devices that communicate through lead-based or leadless means.

In various embodiments, the CRM device detects, receives an alert or otherwise identifies the presence of neural stimulation, and switches from a first to a second set of pacing and/or defibrillation parameters to account for the presence of neural stimulation. It is known that some neural stimulation can alter, among other things, cardiac conduction, contractility and excitability. The use of the second set of parameters accounts for such changes induced by the neural stimulation.

In various embodiments, the neural stimulation device detects, receives an alert or otherwise identifies the presence of the CRM device, and switches from a first to a second set of neural stimulation parameters. CRM therapy captures cardiac tissue with electrical energy. The electrical energy itself can cause problems. An example of switching from a first set of parameter to a second set of parameters includes stimulating a different neural target, or changing a neural stimulation signal parameter, such as amplitude, frequency, burst timing and morphology, to compensate for the CRM therapy. Another example provides a neural stimulation therapy to cooperate with CRM therapy, such as by stimulating an SVC-AO cardiac fat pad to selectively control contractility for the heart, a PV cardiac fat pad associated with an sinoatrial (SA) node to selectively control a sinus rate, and/or an IVC-LA cardiac fat pad associated with an atrioventricular (AV) node to selectively control AV conduction. In humans, the SVC-AO cardiac fat pad is located proximate to a junction between a superior vena cava and an aorta, the PV cardiac fat pad is located proximate to a junction between a right atrium and right pulmonary vein, and the IVC-LA cardiac fat pad is located proximate to a junction between an inferior vena cava and left atrium. Because fat pad ganglia form part of the efferent pathway, stimulation of cardiac fat pads directly effects cardiac tissue. For example, stimulating the parasympathetic efferents can selectively affect rate, and conduction. Stimulation of the parasympathetic pathway also has post-ganglionic inhibition of sympathetic outflow. The cardiac fat pads can be stimulated with epicardial leads with electrodes placed in or near the target fat pad, with intravascularly-fed leads to transvascularly stimulate the target fat pad from within the vessel, and intravascularly fed leads to pierce through a vessel wall into the target fat pad. Neural pathways, such as the vagus nerve trunk and vagal cardiac branches, for example, can be stimulated using a nerve cuff, using an intravascularly-fed leads to transvascularly stimulate the neural target from within the vessel, and intravascularly-fed leads to pierce through a vessel wall into position proximate to a neural target. Baroreceptors within blood vessel walls can be stimulated using an intravascularly-fed lead and a stent-like electrode positioned proximate to the target baroreceptors.

According to various embodiments, the CRM device identifies the presence of neural stimulation (e.g. detects the neural stimulation or is alerted by the neural stimulation device). When neural stimulation is identified the device switches from its normal mode to a "neural stimulation mode." In this mode, the device uses alternate settings for parameters such as V-V interval, A-V interval, anti-tachycardia pacing (ATP) rate, defibrillation threshold, etc. to adapt to the presence of neural stimulation. The second set of parameters are independently programmable in some embodiments. Some embodiments automatically relate the second set of parameters to the baseline parameters.

Since neural stimulation can alter cardiac conduction and excitability. Therefore, the appropriate CRM settings during neural stimulation may be different from the appropriate settings in the absence of neural stimulation. The present subject matter allows the CRM and neural stimulation devices to continuously provide appropriate therapy.

Various embodiments provide a system, either in one device or in more than one device, with capabilities to provide CRM and NS therapy, and with the capability to automatically adjust pacing and defibrillation parameters during neural stimulation to account for altered cardiac conditions. During neural stimulation, some embodiments switch to an alternate set of CRM parameters, compensating for cardiac changes caused by neural stimulation. Therefore, the system has two sets of pacing and defibrillation parameters. The parameters in the sets can be mutually or partially exclusive of each other. The parameters of one set can be a subset of the parameters in another. The sets can include the same parameters, but different values for one or more of the parameters. The second set could be independently programmable or automatically related to the baseline parameters.

FIG. 1 illustrates a system 100 including an implantable medical device (IMD) 101 and a programmer 102, according to various embodiments of the present subject matter. Various embodiments of the IMD 101 include neural stimulator functions only, various embodiments include CRM functions only, and various embodiments include a combination of NS and CRM functions. The IMD can be designed to deliver other therapies, such as drug therapies. The IMD and programmer are capable of wirelessly communicating data and instructions. In various embodiments, for example, the programmer and IMD use telemetry coils to wirelessly communicate data and instructions. Thus, the programmer can be used to adjust the programmed therapy provided by the IMD, and the IMD can report device data (such as battery and lead resistance) and therapy data (such as sense and stimulation data) to the programmer using radio telemetry, for example.

FIG. 1 illustrates an implantable medical device (IMD). Aspects of the present subject matter can be practiced using external devices. FIG. 1 also illustrates that IMD communicating with a programmer. The IMD can also wirelessly communicate directly with a personal digital assistant or other electronic device such as would be used in an advanced patient management (APM) system, which can organize and perform calculations based on recorded data, and later provide the data to a programmer.

Figure 2:
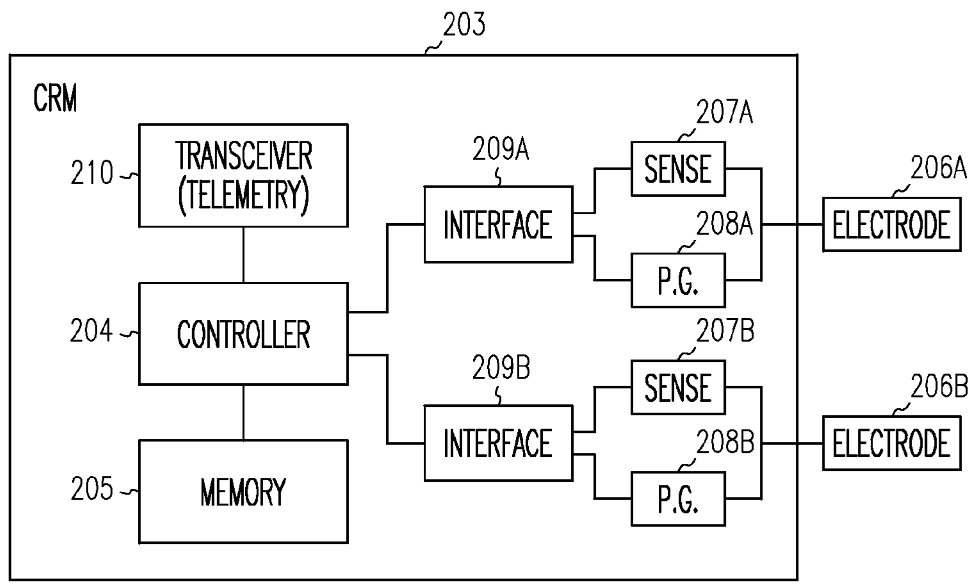
FIG. 2 illustrates an embodiment of CRM device, such as can be used in an IMD in the system of FIG. 1.

FIG. 2 illustrates an embodiment of CRM device 203, such as can be used in an IMD in the system of FIG. 1. The illustrated device 203 includes a controller 204 connected to a memory 205. The figure further illustrates electrodes 206A and 206B connected to the device. According to the illustration, the electrodes 206A and 206B are connected to sense modules 207A and 207B to sense electrical signal at the electrode, and pulse generators 208A and 208B to generate stimulation signals to the electrodes. The controller 204 is connected to the sense modules 207A and 207B and the pulse generator modules 208A and 208B via interfaces 209A and 209B.

The memory includes data and instructions. The controller is adapted to access and operate the instructions to perform various functions within the device, including programmed CRM therapies. The memory 205 includes a plurality of parameters that are used to control the delivery of the therapy. The plurality of parameters are organized into at least two sets. A programmed therapy can be performed using either of the at least two sets of parameters. In various embodiments, the controller operates on the instructions to deliver a therapy, such as bradycardia pacing or defibrillation, of a CRM therapy type is delivered. The controller identifies whether a therapy of a second therapy type, such as a neural stimulation therapy, is present to affect the CRM therapy. Delivery of the CRM therapy is controlled based on the presence of the neural stimulation therapy type. Some embodiments deliver the CRM therapy using one set of parameters in the presence of a neural stimulation therapy and deliver the CRM therapy using another set of parameters when the neural stimulation therapy is not present.

A transceiver 210 is connected to the controller 204. The CRM device is capable of wireless communicating with a programmer, for example, using the transceiver 210. For example, various embodiments use telemetry coils to wirelessly communicate data and instructions. In other embodiments, communication of data and/or energy is by ultrasonic means.

Figure 3:
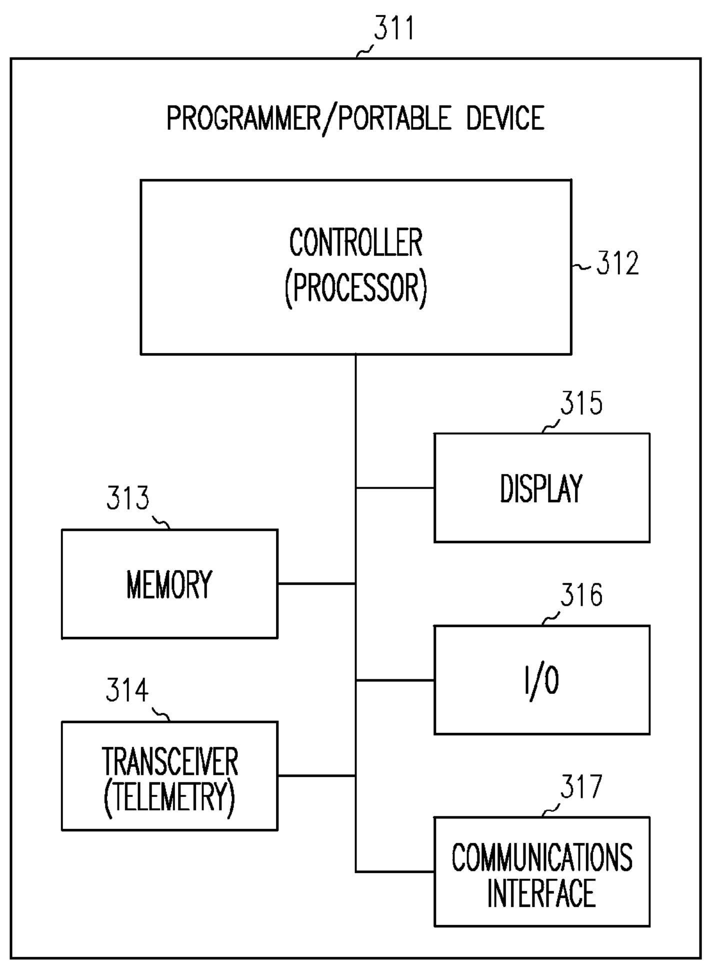
FIG. 3 illustrates a programmer, such as the programmer illustrated in the system of FIG. 1, or other external device to communicate with the implantable medical device(s), according to various embodiments.

FIG. 3 illustrates a programmer 311, such as the programmer 102 illustrated in the system of FIG. 1, or other external device to communicate with the implantable medical device (s), according to various embodiments of the present subject matter. An example of another external device includes Personal Digital Assistants (PDAs) or personal laptop and desktop computers in an Advanced Patient Management (APM) system. The illustrated device includes controller circuitry 312 and a memory 313. The controller circuitry is capable of being implemented using hardware, software, and combinations of hardware and software. For example, according to various embodiments, the controller circuitry includes a processor to perform instructions embedded in the memory to perform a number of functions, including communicating data and/or programming instructions to the implantable devices. The illustrated device 311 further includes a transceiver 314 and associated circuitry for use to communicate with an implantable device. Various embodiments have wireless communication capabilities. For example, various embodiments of the transceiver and associated circuitry include a telemetry coil for use to wirelessly communicate with an implantable device. The illustrated device 311 further includes a display 315, input/output (I/O) devices 316 such as a keyboard or mouse/pointer, and a communications interface 317 for use to communicate with other devices, such as over a communication network.

The programmer is able to program at least some of the parameters in one of the parameter sets used by the IMD to provide the therapy. In some embodiments, the IMD automatically determines the second set of parameters as a function of the programmed first set of parameters. In various embodiments, at least some of the parameters in both a first and second set of parameters is programmable.

Figure 4:
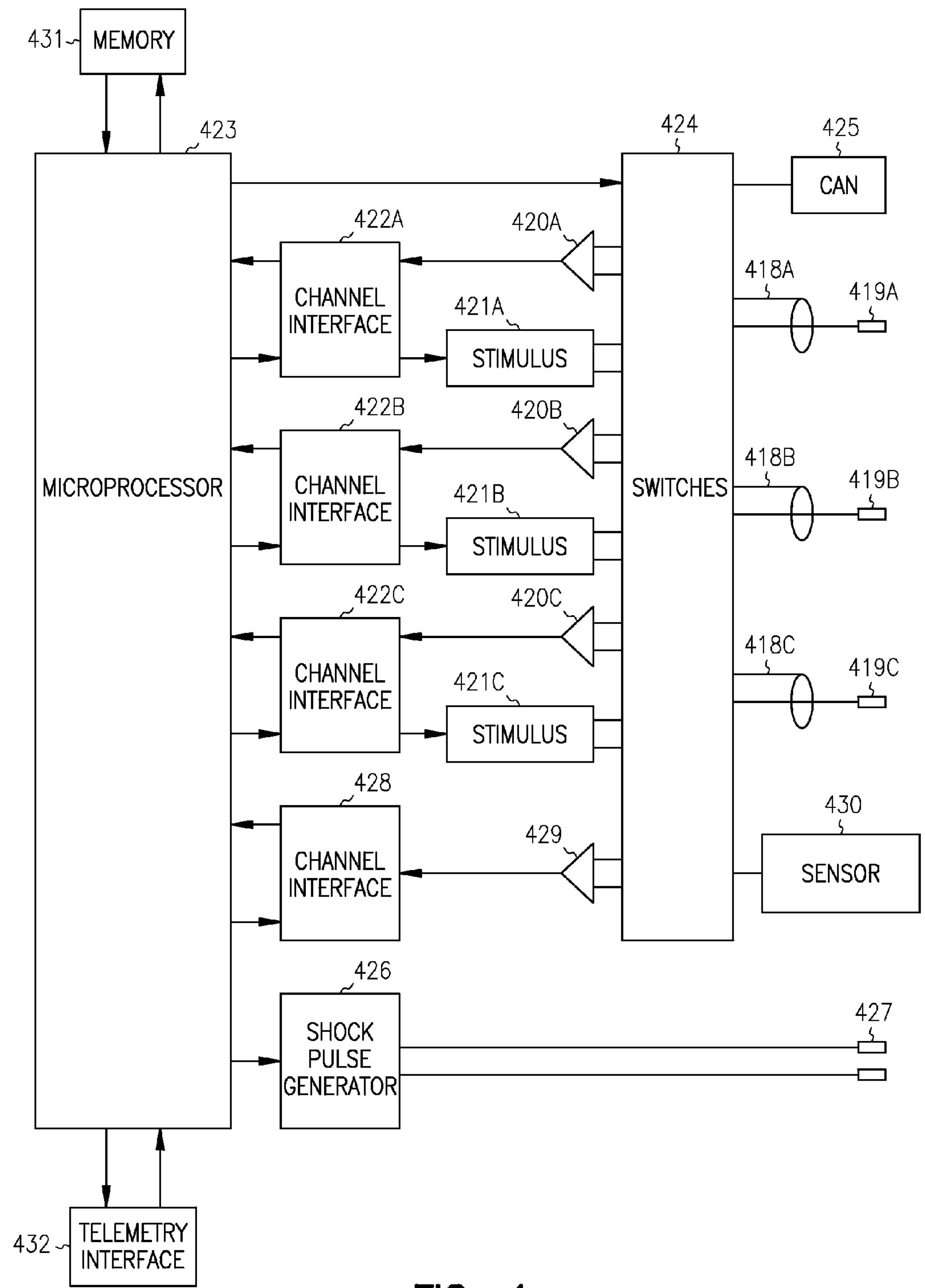
FIG. 4 illustrates a system diagram of an embodiment of an implantable medical device configured for multi-site stimulation and sensing.

FIG. 4 illustrates a system diagram of an embodiment of an implantable medical device configured for multi-site stimulation and sensing. This diagram provides another example of an IMD capable of performing a number of CRM type of therapies. Pacing, as used in the discussion of this figure, relates to electrical stimulation. In various embodiments, the stimulation for a given channel includes stimulation to capture myocardia, neural stimulation or both pacing and neural stimulation. Three examples of sensing and pacing channels are designated "A" through "C". The illustrated channels comprise bipolar leads with ring electrodes 418A-C and tip electrodes 419A-C, sensing amplifiers 420A-C, pulse generators 421A-C, and channel interfaces 422A-C. Each of these channels thus includes a stimulation channel extending between the pulse generator, the electrode and a sensing channel extending between the sense amplifier and the electrode. The channel interfaces 422A-C communicate bidirectionally with microprocessor 423, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry detects a chamber sense, either an atrial sense or ventricular sense, when an electrogram signal (i.e., a voltage sensed by an electrode representing cardiac electrical activity) generated by a particular channel exceeds a specified detection threshold. Algorithms, including a number of adjustable parameters, used in particular stimulation modes employ such senses to trigger or inhibit stimulation, and the intrinsic atrial and/or ventricular rates can be detected by measuring the time intervals between atrial and ventricular senses, respectively. The AV conduction can be measured by measuring a time interval between atrial and ventricular intrinsic events.

The switching network 424 is used to switch the electrodes to the input of a sense amplifier in order to detect intrinsic cardiac activity and to the output of a pulse generator in order to deliver stimulation. The switching network also enables the device to sense or stimulate either in a bipolar mode using both the ring and tip electrodes of a lead or in a unipolar mode using only one of the electrodes of the lead with the device housing or can 425 serving as a ground electrode or another electrode on another lead serving as the ground electrode. A shock pulse generator 426 is also interfaced to the controller for delivering a defibrillation shock via a pair of shock electrodes 427 to the atria or ventricles upon detection of a shockable tachyarrhythmia. Channel interface 428 and sense amplifier 429 provide a connection between the microprocessor and the switch to receive a sensed signal from a sensor 430 for use to detect a second therapy type such as a neural stimulation therapy.

The controller or microprocessor controls the overall operation of the device in accordance with programmed instructions and a number of adjustable parameters stored in memory 431, including controlling the delivery of stimulation via the channels, interpreting sense signals received from the sensing channels, and implementing timers for defining escape intervals and sensory refractory periods. The controller is capable of operating the device in a number of programmed stimulation modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited stimulation modes utilize escape intervals to control pacing in accordance with sensed intrinsic activity such that a stimulation pulse is delivered to a heart chamber during a cardiac cycle only after expiration of a defined escape interval during which no intrinsic beat by the chamber is detected. Escape intervals for ventricular stimulation can be restarted by ventricular or atrial events, the latter allowing the pacing to track intrinsic atrial beats. A telemetry interface 432 is also provided which enables the controller to communicate with an external programmer or remote monitor. Rather than or in addition to interface 428, sense amplifier 429 and sensor 430, some embodiments receive an alert or other communication through the telemetry interface or through other communication means to identify the presence of another type of therapy.

Figure 5:
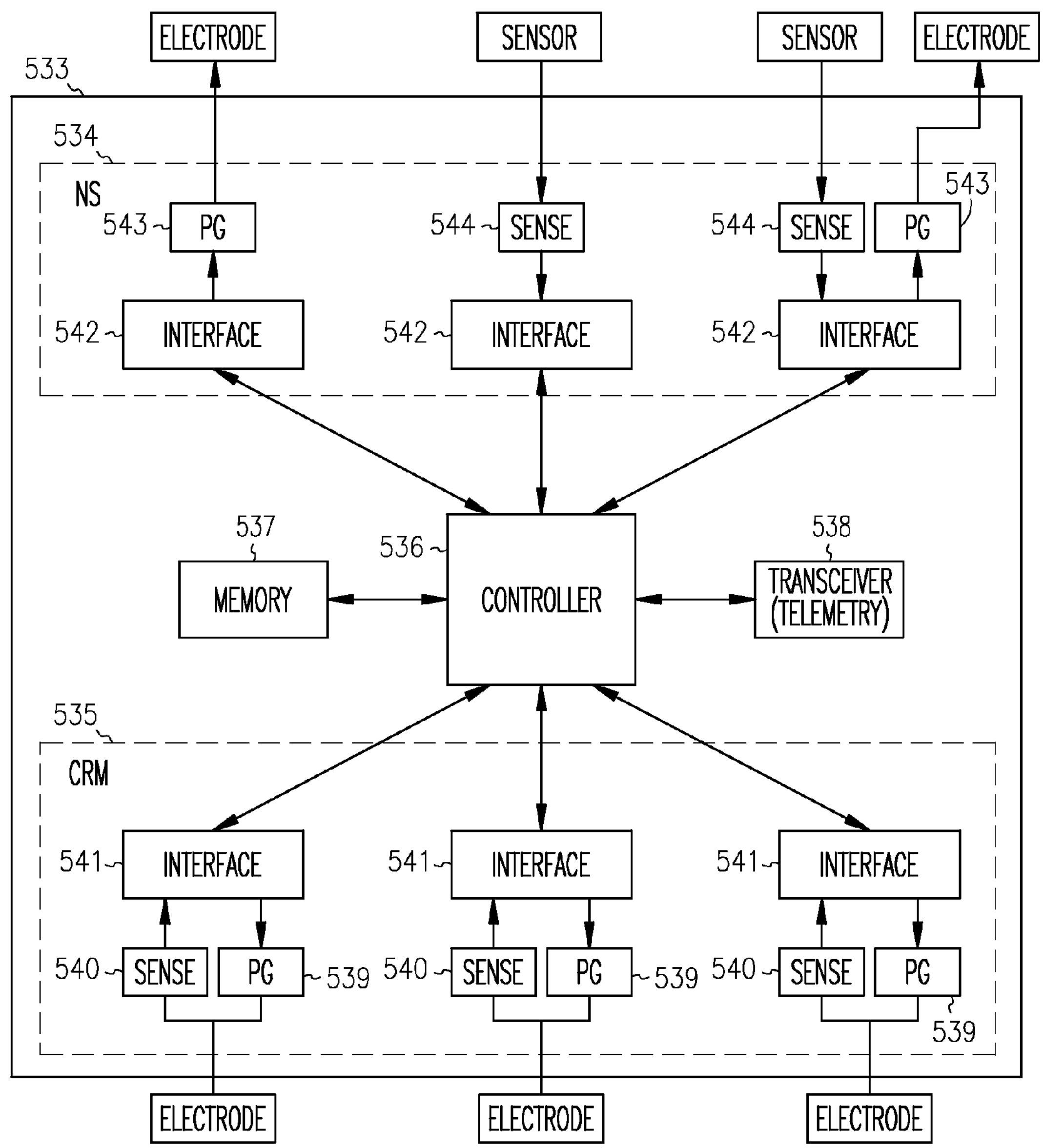
FIG. 5 illustrates an implantable medical device (IMD) such as shown in FIG. 1 having a neural stimulation (NS) component and cardiac rhythm management (CRM) component, according to various embodiments.

FIG. 5 illustrates an implantable medical device (IMD) 533 such as shown at 101 in FIG. 1 having a neural stimulation (NS) component 534 and cardiac rhythm management (CRM) component 535, according to various embodiments of the present subject matter. The illustrated device 533 includes a controller 536 and a memory 537. According to various embodiments, the controller includes hardware, software, or a combination of hardware and software to perform the baroreceptor stimulation and CRM functions. For example, the programmed therapy applications, including a plurality of parameters organized in at least two parameter sets, discussed in this disclosure are capable of being stored as computer-readable instructions embodied in memory and executed by a processor. According to various embodiments, the controller includes a processor to execute instructions embedded in memory to perform the baroreceptor stimulation and CRM functions. The illustrated device 533 further includes a transceiver 538 and associated circuitry for use to communicate with a programmer or another external or internal device. Various embodiments include a telemetry coil.

The CRM therapy section 535 includes components, under the control of the controller, to stimulate a heart and/or sense cardiac signals using one or more electrodes. The CRM therapy section includes a pulse generator 539 for use to provide an electrical signal through an electrode to stimulate a heart, and further includes sense circuitry 540 to detect and process sensed cardiac signals. An interface 541 is generally illustrated for use to communicate between the controller 536 and the pulse generator 539 and sense circuitry 540. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 534 includes components, under the control of the controller, to stimulate a baroreceptor and/or sense ANS parameters associated with nerve activity or surrogates of ANS parameters such as blood pressure and respiration. Three interfaces 542 are illustrated for use to provide ANS therapy. However, the present subject matter is not limited to a particular number interfaces, or to any particular stimulating or sensing functions. Pulse generators 543 are used to provide electrical pulses to an electrode for use to stimulate a baroreceptor site. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 544 are used to detect and process signals from a sensor, such as a sensor of nerve activity, blood pressure, respiration, and the like. The interfaces 542 are generally illustrated for use to communicate between the controller 536 and the pulse generator 543 and sense circuitry 544. Each interface, for example, may be used to control a separate lead. Various embodiments of the NS therapy section only include a pulse generator to stimulate baroreceptors.

According to various embodiments, the lead(s) and the electrode(s) on the leads are physically arranged with respect to the heart in a fashion that enables the electrodes to properly transmit pulses and sense signals from the heart, and with respect to neural targets to stimulate, and in some embodiments sense neural traffic from, the neural targets. Examples of neural targets include both efferent and afferent pathways, such as baroreceptors, nerve trunks and branches such as the vagus nerve, and cardiac fat pads, to provide a desired neural stimulation therapy. As there may be a number of leads and a number of electrodes per lead, the configuration can be programmed to use a particular electrode or electrodes.

The leads of the device include one or more leads to provide CRM therapy, such as atrial pacing, right and/or left ventricular pacing, and/or defibrillation. The device also contains at least on neural stimulation lead which is placed in an appropriate location. Some embodiments perform neural stimulation and CRM therapy using the same lead. Examples of neural stimulation leads include: an expandable stimulation lead placed in the pulmonary artery in proximity of a high concentration of baroreceptors; an intravascularly-fed lead placed proximate to a cardiac fat pad to transvascularly stimulate the fat pad; an epicardial lead with an electrode placed in or proximate to the fat pad; a cuff electrode placed around the aortic, carotid, or vagus nerve; and an intravascularly-fed lead placed to transvascularly stimulate the aortic, carotid or vagus nerve. Other lead placements to stimulate other neural targets may be used.

The controller controls delivery of the electrical pulses using a plurality of parameters for at least one programmed electrical therapy of a first electrical therapy type. The controller is adapted to determine when a therapy of a second electrical therapy type is applied, which can be sensed or other communicated via an alert signal. The controller provides electrical therapy for the first electrical therapy type using a first set of parameters when the therapy of the second electrical therapy type is present to affect the at least one programmed electrical therapy for the first electrical therapy type, and provides electrical therapy using a second set of parameters when the therapy of the second electrical therapy type is not present.

In some embodiments, the first electrical therapy type is a CRM type of therapy, and the second electrical therapy is a neural stimulation type of therapy. There are a number of therapies of a CRM type. Examples include ventricular defibrillation, atrial defibrillation, pacing such as bradycardia and tachycardia pacing, and cardiac rhythm management therapy. In some embodiments, the second electrical therapy type is a neural stimulation (NS) type of therapy. There are a number of therapies of an NS type. Examples include anti-hypertension therapy, therapy for a myocardial infarction, and stimulation to selectively control cardiac conduction and contractility. In other embodiments, the first electrical therapy type is an NS type and the second electrical therapy type is a CRM type.

A plurality of parameters are used by algorithms performed by the controller to deliver the desired therapy. Often, these parameters are adjustable. A programmer, for example, is able to adjust parameters in an IMD. The present subject matter organizes the parameters into at least two sets for a given therapy of the first type. The parameter set used depends on whether the second therapy type is present. The different parameter sets can represent a different value for at least one of the parameters, or can represent at least one different parameter. The different parameter sets can represent different pacing modes, such as atrial pacing (AOO, AAI), ventricular pacing (VVI, VOO), and or dual chamber pacing (DDI, DDD, VDD), for example. Thus, changing the parameter set can change the pacing mode. Additionally, changing the parameter set can change values for parameters for a particular pacing mode, such as base rate, upper rate, AV interval, ventricular refractory and ventricular blanking in a DDD pacing mode.

In some embodiments, the first electrical therapy type is a NS type of therapy, and the second electrical therapy is a CRM type of therapy. Examples of parameters for neural stimulation include parameters that control location of the neural target, and that control amplitude, frequency, burst timing (such as burst frequency and burst duration), and morphology.

Figure 6:
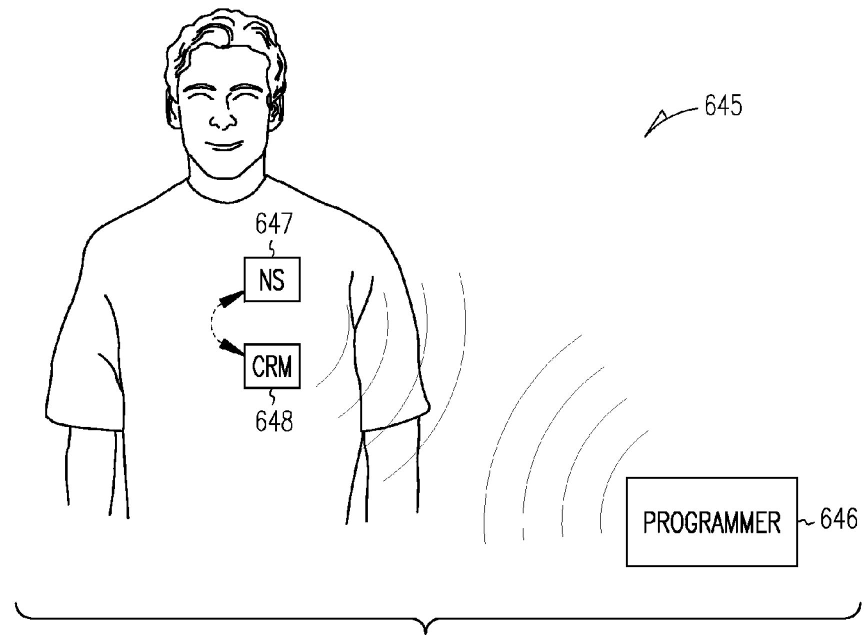
FIG. 6 illustrates a system including a programmer, an implantable neural stimulator (NS) device and an implantable cardiac rhythm management (CRM) device, according to various embodiments.

FIG. 6 illustrates a system 645 including a programmer 646, an implantable neural stimulator (NS) device 647 and an implantable cardiac rhythm management (CRM) device 648, according to various embodiments of the present subject matter. Various aspects involve a method for communicating between an NS device and a CRM device or other cardiac stimulator. This communication allows one of the devices 647 or 648 to deliver more appropriate therapy (i.e. more appropriate NS therapy or CRM therapy) based on data and/or communication signals received from the other device. Some embodiments provide on-demand communications. The illustrated NS device and the CRM device are capable of wirelessly communicating with each other, and the programmer is capable of wirelessly communicating with at least one of the NS and the CRM devices. For example, various embodiments use telemetry coils to wirelessly communicate data and instructions to each other. In other embodiments, communication of data and/or energy is by ultrasonic means. In some embodiments, a lead provides a hardwired communication path between the two devices. An example of a CRM device is illustrated in FIGS. 3 and 4.

Figure 7:
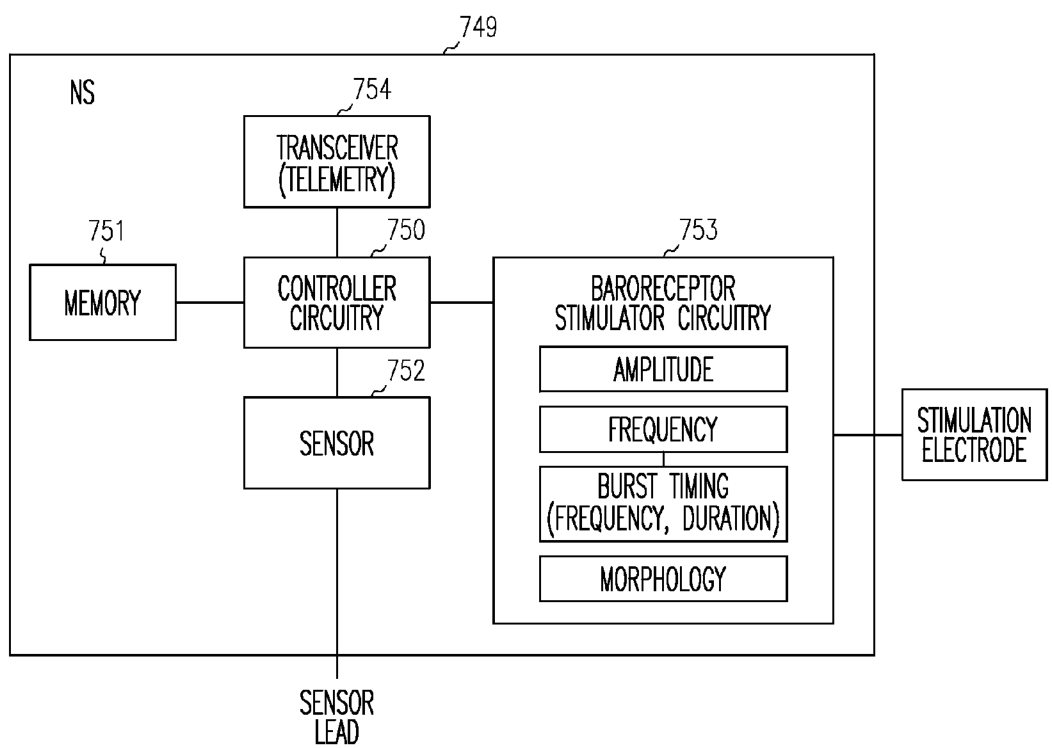
FIG. 7 illustrates an implantable neural stimulator (NS) device such as can be incorporated as the IMD in the system of FIG. 1 or as the neural stimulator in the system of FIG. 6, according to various embodiments of the present subject matter.

FIG. 7 illustrates an implantable neural stimulator (NS) device 749 such as can be incorporated as the IMD 101 in the system 100 of FIG. 1 or as the neural stimulator 647 in the system 645 of FIG. 6, according to various embodiments of the present subject matter. The illustrated neural stimulator 749 includes controller circuitry 750 connected to a memory 751, a sensor 752, a neural stimulation circuitry 753, and a transceiver 754. An electrode is connected to the stimulator circuitry 753. The memory includes instructions or algorithms operated on by the controller and further includes parameters for use in the algorithms to provide the desired neural stimulation therapy. Some embodiments use the sensor, such as a neural sensor or other physiologic sensor like a heart rate sensor, to provide feedback for the neural stimulation. The stimulator circuitry is adapted to adjust parameters of the neural stimulation signal transmitted to the electrode. According to various embodiments, one or more of the amplitude, the frequency, the morphology and the burst timing (frequency and duration of bursts) are capable of being adjusted. The parameters in the memory are organized into parameter sets to selectively change the neural stimulation, such as by adjusting one or more of the parameters for the neural stimulation signal, depending on whether another therapy type is present.

Figure 8:
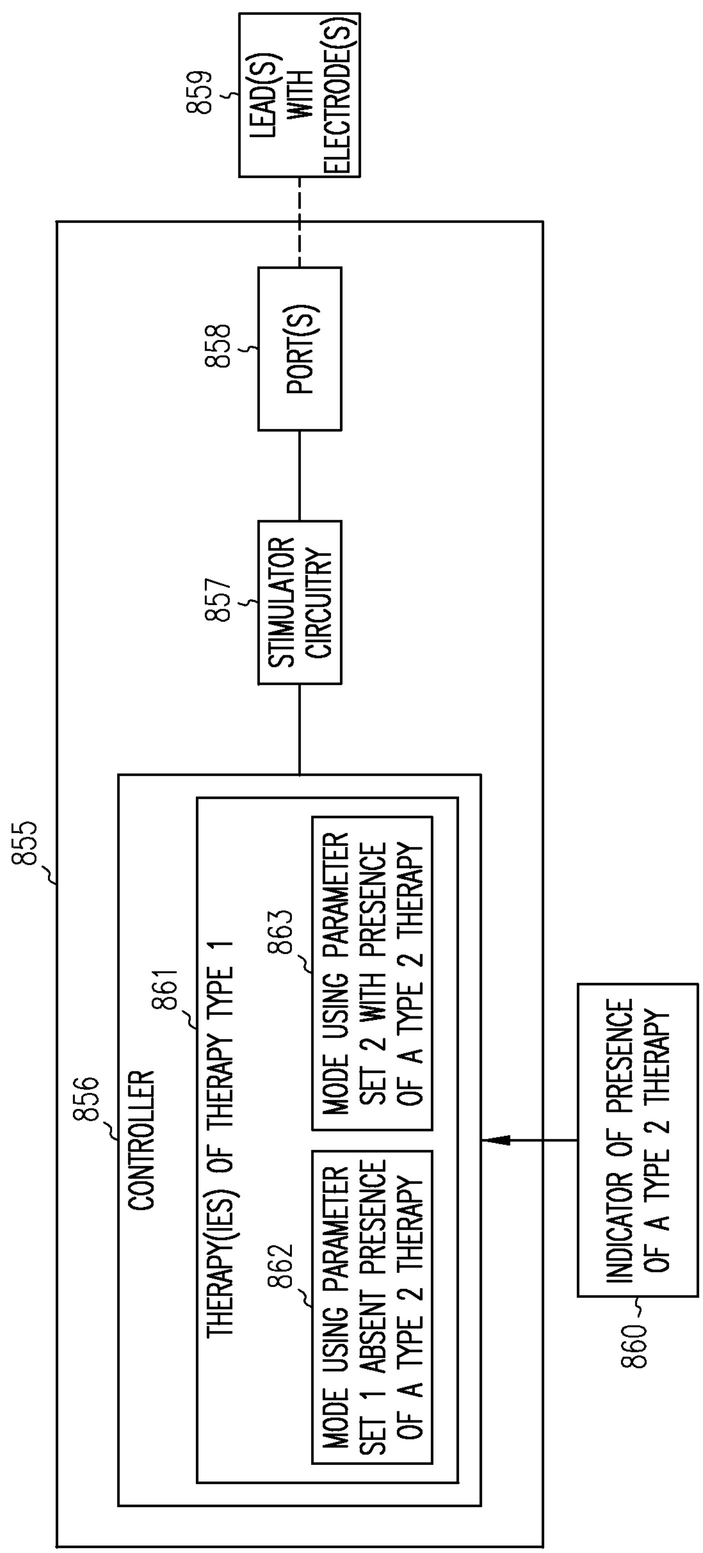
FIG. 8 illustrates a device, according to various embodiments, such as the IMD illustrated in FIG. 1, for example.

FIG. 8 illustrates a device, according to various embodiments of the present subject matter, such as the IMD illustrated in FIG. 1, for example. The illustrated device 855 is adapted to provide a first type of therapy, and includes a controller 856 connected to stimulator circuitry 857 to provide therapy. At least one port 858 is connected to the stimulator circuitry 857. The port(s) 858 are adapted to connect with at least one lead 859, with each lead including at least one electrode. The lead(s) and electrode(s) are positioned to provide a desired therapy. Each port provides a communication channel to an electrode.

The controller is adapted to receive an indicator of the presence of a second type of therapy 860. The controller is adapted to provide at least one therapy of the first therapy type 861, and is able to operate in two modes. The controller enters one therapy mode 862 which uses a first parameter set to provide the therapy of the first type when the second type of therapy is not present. The controller enters another therapy mode 863 which uses a second parameter set to provide the therapy of the first type when the second type of therapy is present. Thus, even if the therapy of the second type is intermittent in nature, the device is able to continue to deliver the first type of therapy.

Figure 9:
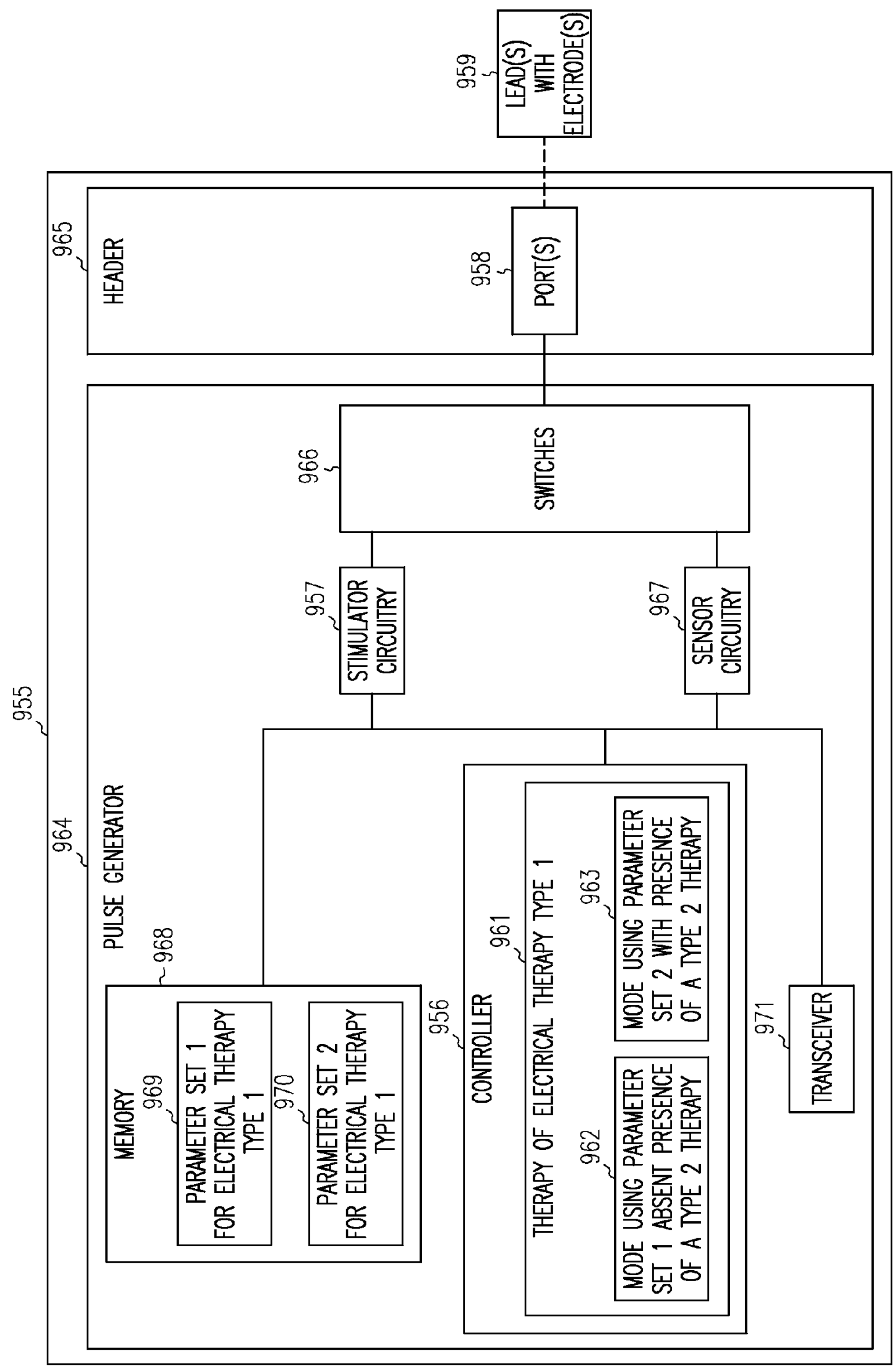
FIG. 9 illustrates a device, according to various embodiments, such as the IMD illustrated in FIG. 1, for example.

FIG. 9 illustrates a device, according to various embodiments of the present subject matter, such as the IMD illustrated in FIG. 1, for example. The illustrated device 955 includes a header section 965 and a pulse generator section 964. The pulse generator section includes the processing circuitry, and the header provides a physical interface to receive leads 959 and further provides electrical interfaces via ports to provide communication channels to each lead electrode.

The illustrated device 955 is adapted to provide a first type of therapy, and includes a controller 956 connected to stimulator circuitry 957 to provide therapy. At least one port 958 is connected to the stimulator circuitry 957 via switches 966. Sensor circuitry 967 is also connected to the at least one port 958 via the switches 966. The switches are used to allow the same communication channel to be used for both stimulation and sensing. The sensor circuitry 967 is connected to the controller 956.

The device 955 further includes memory 968, which includes instructions and a plurality of adjustable parameters to control the therapy. As illustrated, the parameters are organized into two parameter sets 969 and 970. The controller receives an indicator of the presence of a second type of therapy, such as a detected therapy via the sensor circuitry 967 and/or a communicated signal via transceiver 971. The controller is adapted to provide at least one therapy of the first therapy type 961, and is able to operate in two modes. The controller enters one therapy mode 962 which uses a first parameter set 969 to provide the therapy of the first type when the second type of therapy is not present. The controller enters another therapy mode 963 which uses a second parameter set 970 to provide the therapy of the first type when the second type of therapy is present.

The present subject matter is capable of automatically adjusting parameters used to deliver therapy of a first type in response to whether therapy of a second type is present. The present subject matter is also capable of automatically adjusting parameters used to deliver therapy of the first type based on the intensity of the therapy of the second type. Such embodiments can be based on one or more threshold intensities that define different intensity levels. Each intensity level can be associated with a parameter set. Some embodiments adjust the parameters proportionally to the intensity of the second therapy. The parameter adjustments can be linearly or nonlinearly related to the intensity change for the therapy of the second type. The parameter set used for the therapy of the first therapy type can be based solely on whether the therapy of the second therapy type is present, can be based solely on an intensity of the therapy of the second therapy type, and can be based on a combination of whether the therapy of the second therapy type is present and the intensity of the therapy of the second therapy type.

Figure 10:
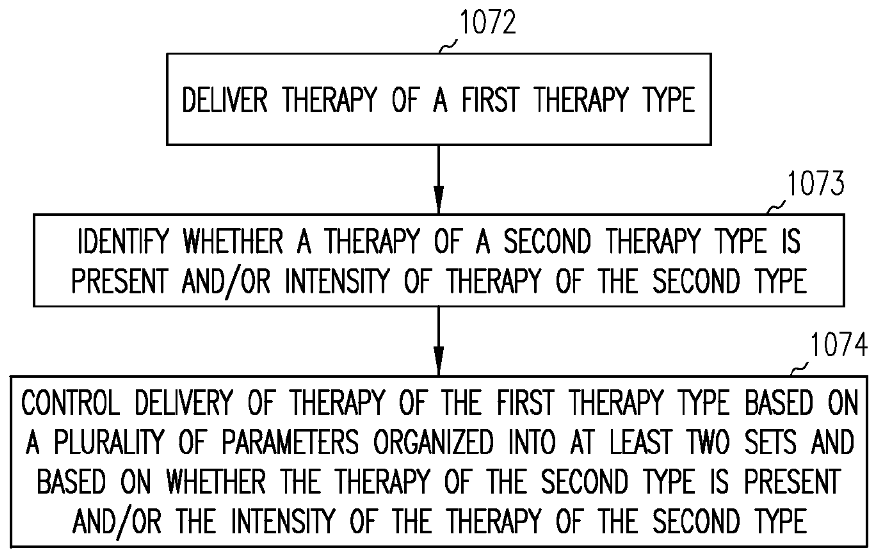
FIG. 10 illustrates a method, according to various embodiments.

FIG. 10 illustrates a method, according to various embodiments. At 1072, a therapy (e.g. bradycardia support pacing) of a first type (e.g. CRM therapy) is delivered. At 1073, it is determined whether a therapy (e.g. neural stimulation of cardiac fat pad) of a second therapy type (neural stimulation therapy) is present and/or the intensity of the therapy of the second type is determined. At 1074, the delivery of therapy of the first therapy type is controlled based on a plurality of parameters organized into at least two sets and based on whether the therapy of the second type is present and/or the intensity of the therapy of the second type.

Figure 11A:
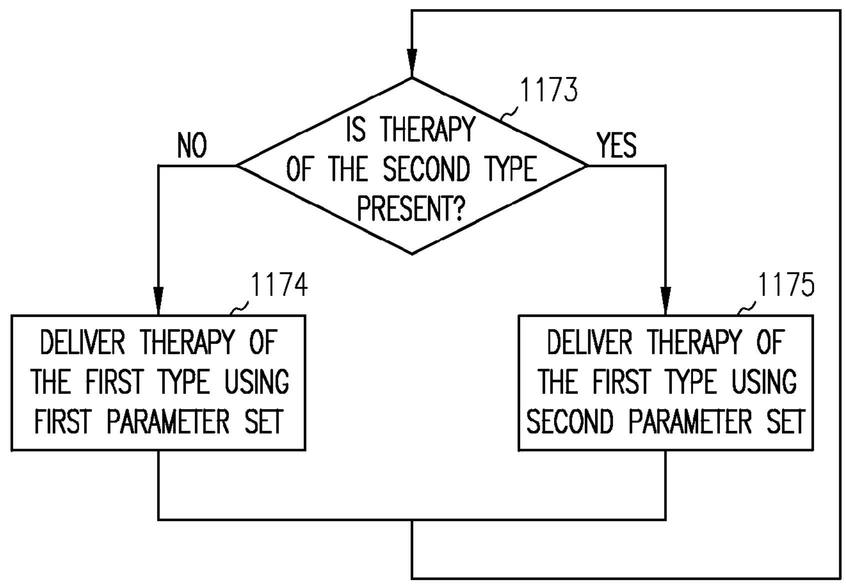
FIG. 11A illustrates a method for controlling delivery of therapy of the first type (e.g. CRM therapy) based on a plurality of parameters organized into at least two sets and based on whether the therapy of the second type (e.g. neural stimulation therapy) is present, according to various embodiments.

FIG. 11A illustrates a method for controlling delivery of therapy of the first type (e.g. CRM therapy) based on a plurality of parameters organized into at least two sets and based on whether the therapy of the second type (e.g. neural stimulation therapy) is present, according to various embodiments. At 1173, it is determined whether the therapy of the second type is present. If the second type of therapy is not present, the process proceeds to 1174 where the therapy of the first type is delivered using a first parameter set 1174. If the second type of therapy is present, the process proceeds to 1175 where the therapy of the first type is delivered using a second parameter set 1175.

Figure 11B:
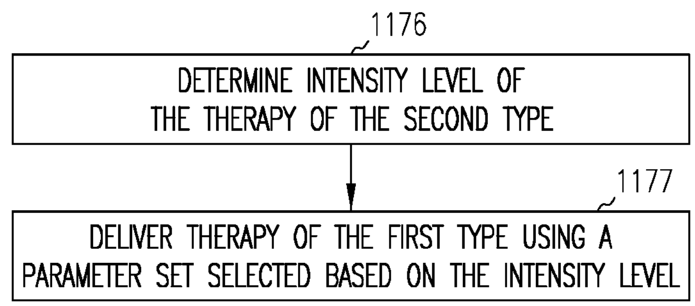
FIG. 11B illustrates a method for controlling delivery of therapy of the first type (e.g. CRM therapy) based the intensity of the therapy of the second type (e.g. neural stimulation therapy), according to various embodiments.

FIG. 11B illustrates a method for controlling delivery of therapy of the first type (e.g. CRM therapy) based the intensity of the therapy of the second type (e.g. neural stimulation therapy), according to various embodiments. At 1176, the intensity level of the therapy of the second type is determined. The determination of the intensity level can be use a few distinct levels separated by threshold values, such as a high and low intensity, or can more precisely quantify the intensity level throughout the continuum from the lowest to highest intensities. At 1177, therapy of the first type is delivered using a parameter set selected based on the intensity level determined at 1176.

Figure 11C:
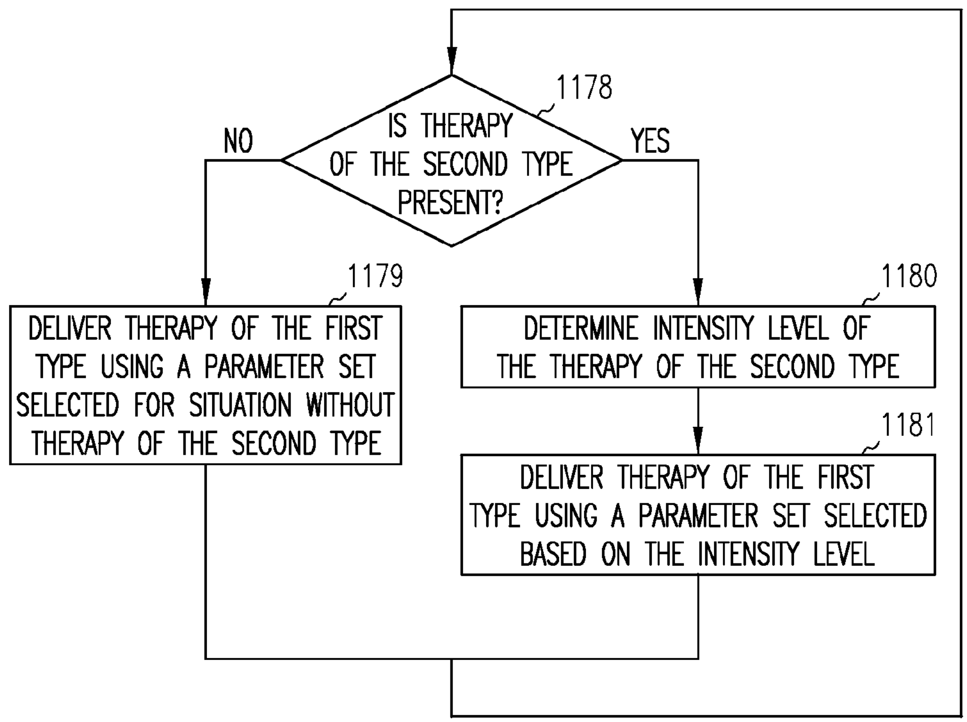
FIG. 11C illustrates a method for controlling delivery of therapy of the first type (e.g. CRM therapy) based on whether the therapy of the second type (e.g. neural stimulation therapy) is present and on the intensity of the therapy of the second type, according to various embodiments.

FIG. 11C illustrates a method for controlling delivery of therapy of the first type (e.g. CRM therapy) based on whether the therapy of the second type (e.g. neural stimulation therapy) is present and on the intensity of the therapy of the second type, according to various embodiments. At 1178, it is determined whether therapy of the second type is present. If the therapy of the second type is not present, the process proceeds to 1179, where therapy of the first type is delivered using a parameter set selected for situations without the therapy of the second type. If the therapy of the second type is present, the process proceeds to 1180 where the intensity level of the therapy of the second type is determined, and to 1181 where the therapy of the first types is delivered using a parameter set selected based on the intensity level.

Figure 12A:
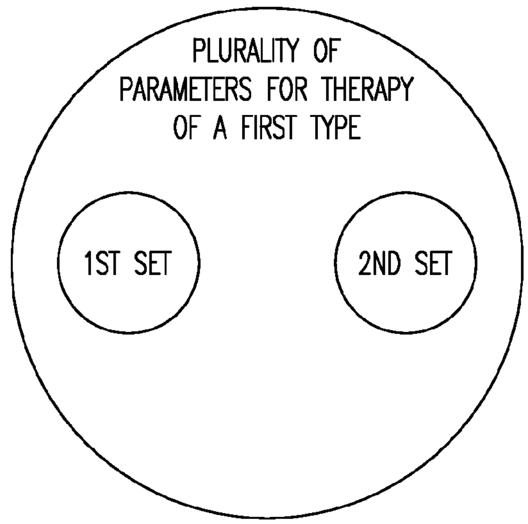
FIGS. 12A, 12B and 12C illustrate plurality of parameters, and further illustrate the first and second sets of parameters, according to various embodiments.
Figure 12B:
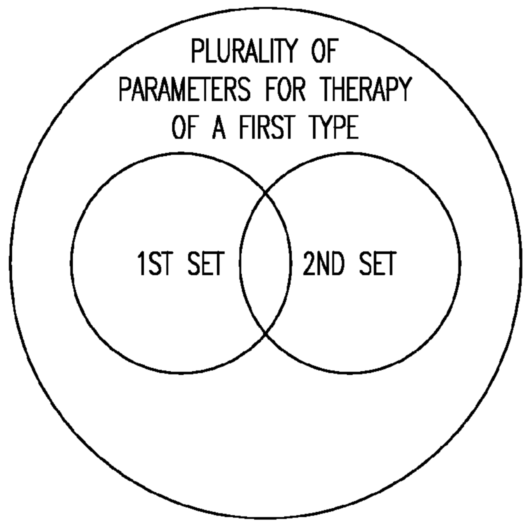
Figure 12C:
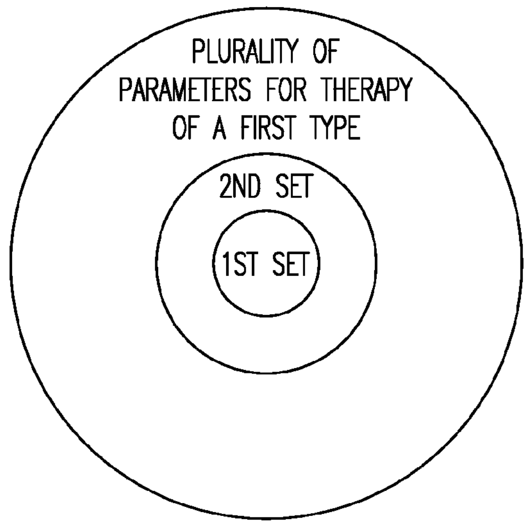

FIGS. 12A, 12B and 12C illustrate plurality of parameters, and further illustrate the first and second sets of parameters, according to various embodiments. FIG. 12A illustrates a first set and a second set in which the sets are exclusive of each other. That is, the sets are defined and organized to be mutually exclusive such that each set includes distinct parameters with respect to the other set. FIG. 12B illustrates a first set and a second set that are at least partially inclusive, being defined and organized to share at least some parameters. FIG. 12C illustrates a first set that is a subset of the second set. In addition to the illustrated relationships between the first and second sets, some embodiments may include sets with the same parameters, where the differences between the parameter sets are provided by different adjustable or programmable values of the parameters.

In some embodiments, all of the adjustable parameters in each parameter set are independently programmable. In some embodiments, the adjustable parameters in one parameter set is programmable, and the adjustable parameters in the other parameter set are automatically adjusted as a function of the values for the parameters in the first parameter set.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. For example, various embodiments combine two or more of the illustrated processes. Two or more sensed parameters can be combined into a composite parameter used to provide a desired CRM therapy. In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. A method, comprising:

delivering a therapy of a first therapy type;

determining an intensity for a therapy of a second therapy type; and controlling delivery of the therapy of the first therapy type based on the intensity of the therapy of the second therapy type, including delivering the therapy of the first therapy type using a parameter set selected based on the intensity of the therapy of the second therapy type.

2. The method of claim 1, further comprising:

determining whether the therapy of the second type is present, delivering therapy of the first type using a parameter set selected for use when the therapy of the second type is not present; and delivering the therapy of the first therapy type using the parameter set selected based on the intensity of the therapy of the second therapy type when the therapy of the second type is present.

3. The method of claim 1, wherein the first therapy type is a cardiac rhythm management therapy and the second therapy type is a neural stimulation therapy.

4. The method of claim 1, wherein the first therapy type is a neural stimulation therapy and the second therapy type is a cardiac rhythm management therapy.

5. The method of claim 1, wherein controlling delivery includes:

controlling delivery of the therapy based on a plurality of parameters organized into a first set and a second set in at least one programmed therapy for the therapy type;

delivering the therapy of the first therapy type using the first set of parameters when the intensity of the therapy of the second therapy type has not reached a threshold value; and delivering the therapy of the first therapy type using the second set of parameters when the intensity of the therapy of the second therapy type reached the threshold value.

6. The method of claim 1, wherein controlling delivery of the therapy of the first therapy type based on the presence of the intensity of the therapy of the second therapy type includes receiving a signal indicative of the intensity of the therapy of the second therapy type.

7. The method of claim 1, wherein:

delivering the therapy of the first therapy type includes using a first implantable device to deliver the therapy of the first therapy type; and delivering the therapy of the second therapy type includes using a second implantable device to deliver the therapy of the second therapy type.

8. The method of claim 1, wherein delivering the therapy of the first therapy type and delivering the therapy of the second therapy type includes using an implantable device to deliver both the therapy of the first therapy type and the therapy of the second therapy type.

9. A method, comprising:

delivering a cardiac rhythm management therapy, wherein delivering the cardiac rhythm management therapy includes delivering myocardial stimulation;

determining an intensity for a neural stimulation therapy; and controlling delivery of the cardiac rhythm management therapy based on the intensity of the neural stimulation therapy, wherein controlling delivery includes delivering the cardiac rhythm management therapy using a parameter set selected based on the intensity of the neural stimulation therapy.

10. The method of claim 9, wherein the neural stimulation therapy includes vagal nerve stimulation.

11. The method of claim 9, wherein the neural stimulation therapy includes stimulation of a baroreceptor site.

12. The method of claim 9, wherein the neural stimulation therapy includes stimulation of a carotid sinus nerve.

13. The method of claim 9, wherein the neural stimulation includes stimulation of a cardiac fat pad.

14. The method of claim 9, wherein the cardiac rhythm management therapy is configured to operate using more than one pacing mode, and delivering the cardiac rhythm management therapy using a parameter set selected based on the intensity of the neural stimulation therapy includes changing pacing modes for the cardiac rhythm management therapy based on the intensity of the neural stimulation therapy.

15. The method of claim 9, wherein the cardiac rhythm management therapy is configured to operate at an anti-tachycardia pacing (ATP) rate, and delivering the cardiac rhythm management therapy using a parameter set selected based on the intensity of the neural stimulation therapy includes changing values for the ATP rate for the cardiac rhythm management therapy based on the intensity of the neural stimulation therapy.

16. The method of claim 9, wherein the cardiac rhythm management therapy is configured to operate using an AV interval or a VV interval, and delivering the cardiac rhythm management therapy using a parameter set selected based on the intensity of the neural stimulation therapy includes changing values for the AV interval or the VV interval based on the intensity of the neural stimulation therapy.

17. The method of claim 9, wherein delivering the cardiac rhythm management therapy includes delivering a defibrillation therapy, and delivering the cardiac rhythm management therapy using a parameter set selected based on the intensity of the neural stimulation therapy includes changing values for a defibrillation threshold for the defibrillation therapy based on the intensity of the neural stimulation therapy.

18. A method, comprising:

delivering a neural stimulation therapy;

determining an intensity for a cardiac rhythm management therapy, wherein the cardiac rhythm management therapy includes myocardial stimulation and determining the intensity includes determining an operation mode for the cardiac rhythm management therapy; and controlling delivery of the neural stimulation therapy based on the cardiac rhythm management therapy, wherein controlling delivery includes delivering the neural stimulation therapy using a parameter set selected based on the intensity of the cardiac rhythm management therapy.

19. The method of claim 18, wherein delivering the neural stimulation therapy using a parameter set selected based on the intensity of the cardiac rhythm management therapy includes delivering the neural stimulation therapy using a neural stimulation amplitude based on the intensity of the cardiac rhythm management therapy.

20. The method of claim 18, wherein delivering the neural stimulation therapy using a parameter set selected based on the intensity of the cardiac rhythm management therapy includes delivering the neural stimulation therapy using a neural stimulation frequency based on the intensity of the cardiac rhythm management therapy.

21. The method of claim 18, wherein delivering the neural stimulation therapy using a parameter set selected based on the intensity of the cardiac rhythm management therapy includes delivering the neural stimulation therapy using neural stimulation burst timing based on the intensity of the cardiac rhythm management therapy.

22. The method of claim 18, wherein delivering the neural stimulation therapy includes delivering vagal nerve stimulation.

23. The method of claim 18, wherein delivering the neural stimulation therapy includes stimulating a baroreceptor site.

24. The method of claim 18, wherein delivering the neural stimulation therapy includes stimulating a carotid sinus nerve.

25. The method of claim 18, wherein delivering the neural stimulation therapy includes stimulating a cardiac fat pad.

* * * * *